United States Patent
Chu et al.

(10) Patent No.: US 10,674,973 B2
(45) Date of Patent: Jun. 9, 2020

(54) RADIATION THERAPY SYSTEM AND METHODS OF USE THEREOF

(71) Applicants: RUSH UNIVERSITY MEDICAL CENTER, Chicago, IL (US); UCHICAGO ARGONNE, LLC, OPERATOR OF ARGONNE NATIONAL LABORATORY, Chicago, IL (US)

(72) Inventors: James Chu, Oak Brook, IL (US); William F. Sensakovic, Orlando, FL (US); Damian Bernard, Naperville, IL (US); Gage Redler, Chicago, IL (US); Steve Wang, Chicago, IL (US)

(73) Assignees: Rush University Medical Center, Chicago, IL (US); UChicago Argonne, LLC, Chicago, IL (US)

( * ) Notice: Subject to any disclaimer, the term of this patent is extended or adjusted under 35 U.S.C. 154(b) by 24 days.

(21) Appl. No.: 15/568,103

(22) PCT Filed: Apr. 21, 2016

(86) PCT No.: PCT/US2016/028595
§ 371 (c)(1),
(2) Date: Oct. 20, 2017

(87) PCT Pub. No.: WO2016/172312
PCT Pub. Date: Oct. 27, 2016

(65) Prior Publication Data
US 2018/0140265 A1 May 24, 2018

Related U.S. Application Data

(60) Provisional application No. 62/152,449, filed on Apr. 24, 2015.

(51) Int. Cl.
*A61B 6/00* (2006.01)
*A61N 5/10* (2006.01)
*A61B 6/06* (2006.01)

(52) U.S. Cl.
CPC ............ *A61B 6/4266* (2013.01); *A61B 6/483* (2013.01); *A61N 5/1049* (2013.01); *A61B 6/06* (2013.01);
(Continued)

(58) Field of Classification Search
CPC ..... A61B 6/4266; A61B 6/483; A61B 5/0091; A61B 8/0825; A61B 6/502; A61B 10/0041; A61N 5/1049
See application file for complete search history.

(56) References Cited

U.S. PATENT DOCUMENTS 6,847,838 B1   1/2005  Macey et al.
7,826,889 B2*  11/2010 David ................. A61B 6/4258
                                                600/3
(Continued)

OTHER PUBLICATIONS

International Search Report and Written Opinion for PCT/US2016/028595 dated Jul. 12, 2016, 11 pgs.

*Primary Examiner* — David P Porta
*Assistant Examiner* — Djura Malevic
(74) *Attorney, Agent, or Firm* — Barnes & Thornburg LLP

(57) ABSTRACT

One aspect of the invention provides a system for radiation treatment of a tumor allowing for imaging of the tumor and a surrounding region during radiation therapy and to methods of using such a system. In one embodiment, the system includes a number of radiation detectors positioned in an array to detect radiation scattered from the tumor and the surrounding region. A 3-dimensional image of the tumor is reconstructed from the 2-dimensional scattered radiation projections.

19 Claims, 10 Drawing Sheets

(52) U.S. Cl.
CPC ....... *A61B 6/583* (2013.01); *A61N 2005/1054* (2013.01)

(56) References Cited

U.S. PATENT DOCUMENTS

| | | | |
|---|---|---|---|
| 8,094,782 B1 * | 1/2012 | Annis | A61B 6/0435 378/37 |
| 8,489,176 B1 * | 7/2013 | Ben-David | A61B 6/4258 600/3 |
| 8,565,860 B2 * | 10/2013 | Kimchy | A61B 5/055 250/363.01 |
| 8,824,630 B2 | 9/2014 | Maurer, Jr. et al. | |
| 8,909,325 B2 * | 12/2014 | Kimchy | G01T 1/161 600/407 |
| 8,915,833 B1 * | 12/2014 | Sahadevan | A61N 5/1027 600/1 |
| 2008/0021300 A1 | 1/2008 | Allison | |
| 2011/0185503 A1 | 8/2011 | Yan | |
| 2011/0284757 A1 * | 11/2011 | Butuceanu | A61N 5/1048 250/389 |
| 2012/0006990 A1 | 1/2012 | Ishikawa | |
| 2013/0060134 A1 | 3/2013 | Eshima et al. | |
| 2015/0087881 A1 | 3/2015 | Miyamoto et al. | |
| 2015/0150460 A1 * | 6/2015 | Krishnaswamy | A61B 1/07 600/408 |
| 2017/0128739 A1 * | 5/2017 | Dilmanian | A61N 5/1045 |
| 2018/0236267 A1 * | 8/2018 | Kuang | A61N 5/1039 |

\* cited by examiner

RADIATION THERAPY SYSTEM AND METHODS OF USE THEREOF

RELATED APPLICATIONS

This application is a National Stage of PCT/US2016/028595, filed Apr. 21, 2016, which claims the benefit of the filing date of U.S. Provisional Patent Application No. 62/152,449, filed Apr. 24, 2015, the contents of which applications are hereby incorporated by reference.

TECHNICAL FIELD

The present invention generally relates to a system for radiation treatment of a tumor allowing for imaging of the tumor and a surrounding region during radiation therapy and to methods of using such a system. In one embodiment, the system includes a number of radiation detectors positioned in an array to detect radiation scattered from the tumor and the surrounding region. A 3-dimensional image of the tumor is reconstructed from the 2-dimensional scattered radiation projections.

BACKGROUND

More than 224,000 people are expected to be diagnosed with lung cancer alone in the U.S. in 2015[1]. With 159,000 deaths expected to result from these new cases, it is the most lethal cancer today. Detecting and treating these patients in early stages of this disease offers the best chance of cure. Stereotactic ablative radiotherapy (SABR) is a new technology for delivering very high radiation dose to a small tumor target volume with high precision. The clinical results from SABR of early lung cancers are very promising with outcome matching that from surgery for both operable and inoperable patients[2,3]. Conducting SABR treatments, however, is tedious and time-consuming, largely due to the need to verify the target position throughout the duration of the treatment. Development of new technologies that can provide rapid and accurate patient verification images is important to the success of SABR program. This is of particular importance given that the number of lung cancers is likely to rise due to an aging population and the success of low-dose CT screening[4,5].

SUMMARY OF THE PREFERRED EMBODIMENTS

One aspect of the present invention provides a system for radiation treatment of a tumor. In one embodiment, the system includes a structure for positioning a patient having the tumor and a radiation source device positioned to deliver a radiation beam upon a region containing the tumor. The system also includes a number of radiation detectors positioned in an array to detect scattered radiation from the region.

Each of the detectors is configured to acquire a 2-dimensional projection dataset from radiation scattered from the region and is operatively connected to a processing unit. The processing unit is configured to receive the 2-dimensional projection dataset from each of the radiation detectors and to generate a 3-dimensional image dataset from the 2-dimensional projection datasets.

Another aspect of the present invention provides a method of treating a patient having a tumor. In one embodiment, the method includes providing a radiation treatment system as disclosed herein. The radiation source is positioned to deliver radiation to the region containing the tumor and a first dose of radiation delivered to the region.

A time series of 2-dimensional projection datasets is generated from radiation scattered from the region and detected by the radiation detectors. A 3-dimensional image data set is generated at each time point of the time series from the 2-dimensional projection datasets generated at that time point. The 3-dimensional image data set at a time point is indicative of the position of the region in relation to the radiation beam at that time point.

The 3-dimensional image data sets generated for at least two time points are compared and any movement of the region in relation to the radiation beam determined on the basis of this comparison. The radiation source or the patient is moved to correct for any movement of the region in relation to the radiation beam and a second radiation dose is delivered to the region.

BRIEF DESCRIPTION OF THE DRAWINGS

FIG. 3(A) Darker (outer) and lighter (inner) materials are water equivalent (solid water and bolus) and lung equivalent (cork), respectively. The dimensions used simulate a 2.8 cm diameter cylindrical tumor oriented so that the incident radiation beam passes through 4 cm of chest wall and 3.1 cm of lung. On the detector side of the phantom, scattered radiation (arrow) passes through 2 cm of lung and 2 cm of chest wall. This geometry approximates that which may be encountered in a lung SABR treatment. FIG. 3(B) Representative MCNP simulated image. FIG. 3(C) 0.5 s, FIG. 3(D) 2.5 s, and FIG. 3(E) 10 s experimental images. The central dark circle is the tumor. The dark and faint rectangles are the chest wall on the treatment beam entrance and exit side, respectively. Contrast-to-noise (CNR) is the image quality metric. These preliminary images demonstrate that (even with a non-optimized system) scatter imaging has the potential to acquire rapid images with temporal resolution and CNR adequate for real-time target tracking during SBRT treatment.

FIG. 4(A) Monte Carlo simulated image with 0.15 cGy delivered to the tumor, pixel size 0.17 mm. (FIG. 4B) is similar to FIG. 4(A) but with pixel averaging image enhancement, pixel size 1.7 mm. Both SNR and CNR improve more than a factor of 12.

In FIG. 8(B) the experimental (5000 MU or 250 second) image can be seen to match closely with the noiseless MCNP simulated image of the same phantom FIG. 8(C).

DETAILED DESCRIPTION OF THE PREFERRED EMBODIMENTS

Definitions

Figure 1:
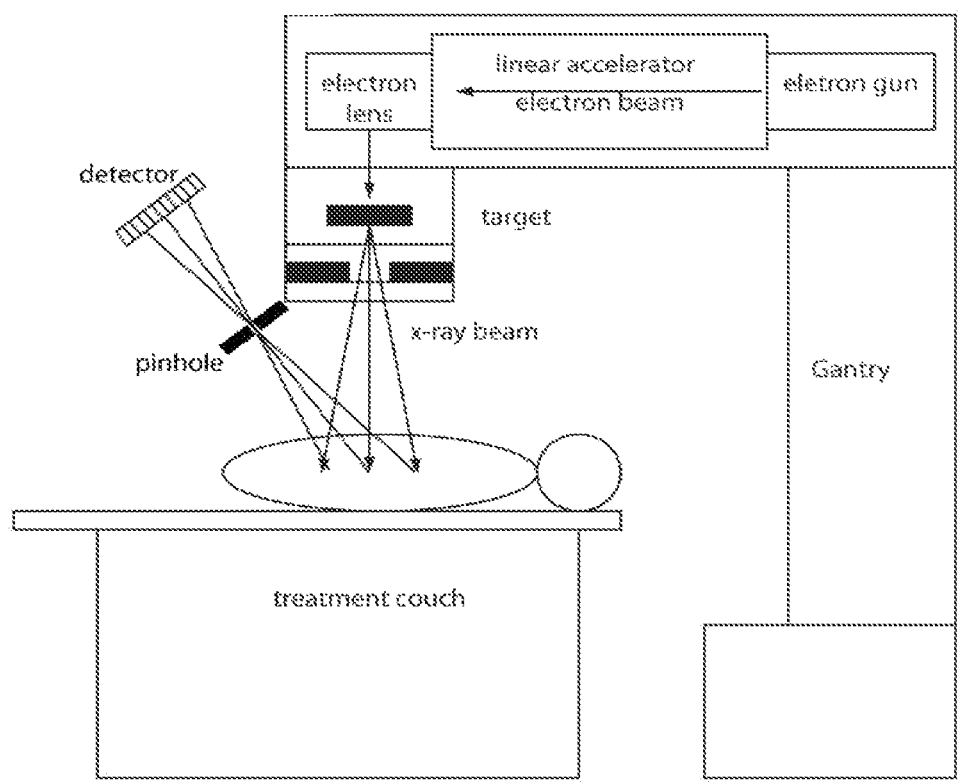
FIG. 1 is a schematic illustration of the proposed scatter imaging system. Only one pinhole camera is shown.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

System for Radiation Treatment of a Tumor

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of apparatus and systems, methods of analysis, or other aspects, are disclosed. It is to be understood that each such disclosed feature or features can be combined with the generalized features discussed, to form a disclosed embodiment of the present invention.

Turning now to FIG. 1. This figure illustrates one embodiment of a radiation treatment system of the present invention. The system includes a structure for positioning a patient to be treated for the presence of a tumor. Here, the patient is illustrated as being positioned on a treatment couch. However, alternative structures are also within the scope of the present invention. All that is required is that the patient is positioned to place the tumor within a radiation beam.

A radiation source, for example, a linear accelerator which generates radiation by bombarding a target with electrons, is positioned to deliver a radiation beam upon a region containing the tumor in the patient positioned on the patient positioning structure. In other embodiments, other sources of radiation suitable for the treatment of tumors may be used.

A plurality of radiation detectors is positioned in an array to detect scattered radiation from the region. In the figure only one such detector is illustrated. However, preferably multiple detectors will be positioned in an array to detect radiation scattered by the region containing the tumor.

Each to the radiation detectors is configured to acquire a 2-dimensional projection dataset from the radiation scattered from the region. Further details of the construction of the detectors are disclosed herein. The radiation detectors are operatively connected to a processing unit which receives a 2-dimensional projection dataset from each of the radiation detectors and generates a 3-dimensional image dataset from the 2-dimensional projection datasets. An image showing the tumor is constructed from the 3-dimensional image dataset.

In one embodiment, the radiation detectors include a pinhole collimator and a radiation detection panel. In other embodiments, the radiation detectors are coded aperture or multi-pinhole cameras, Gamma cameras, parallel hole collimators or Compton cameras.

The system utilizes the scattered radiation from the region of the tumor produced during patient's radiation treatment. Thus, it requires no additional radiation and produces images in real-time without potential side effects. In addition, in preferred embodiments, multiple detectors are placed around the head of the treatment machine, allowing the imaging system to provide 3-D information of the target volume. Unlike transmission imaging used in conventional x-rays, the image contrast from the system is determined by the density and composition of objects within the region of interest rather than the difference in radiation transmission over the region. This offers potentially superior image contrast when compared with that from the MeV x-ray imaging that is widely used in radiation therapy.

Figure 6:
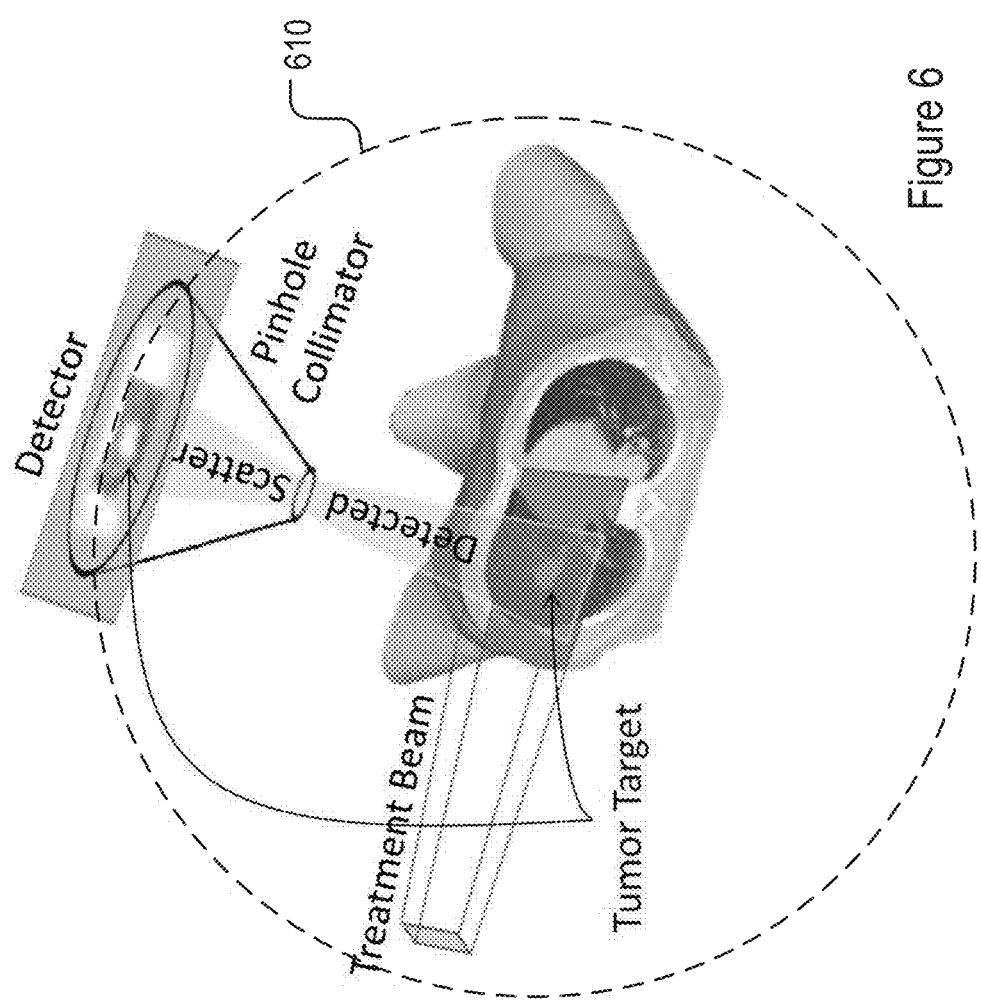
FIG. 6 is a schematic illustration of a scatter imaging system for Stereotactic Body Radiation Therapy (SBRT).

In one embodiment, the system includes at least 3 radiation detectors. In other embodiments, the system includes, for example, 3 to 60, or 3 to 30 or 3 to 20 or 10 to 30 or 10 to 20 radiation detectors. The detectors are positioned to detect radiation scattered from the region containing the tumor. For example, the detectors may be positioned to place the pinhole of the pinhole collimator on the surface defined by a sphere centered on the center of the tumor. Referring to FIG. 6, a plurality of detectors may be disposed on the surface 610 of a sphere. In certain embodiments, radiation detectors are pinhole collimators and the collimators are positioned and aligned such that the angle between the center of the radiation beam and the center of the collimator is at an angle of between 15 and 165, or 20 and 150 or 25 and 10 degrees. However, other configurations are within the scope of the present invention. All that is required is that the radiation detectors are positioned to allow for the collection of scattered radiation sufficient for the determination of the position of the tumor.

In one embodiment, the radiation detectors are positioned to achieve a 1:1 imaging geometry. Here, where the detectors are pinhole collimator detectors, the pinholes of the pinhole collimators are positioned at the same distance positioned from the center of the tumor, for example, at a distance of between 12 and 25 cm, or between 15 and 20 cm. The distance from the pinhole to the surface of the detector chip is the same as the distance from the pinhole to the center of the tumor. In one embodiment, the axes of the collimators are aligned to extend through the center of the tumor.

The pinhole camera design is primarily dictated by the lack of effective optics technology for focusing high energy x-ray radiation. With this imaging modality, the throughput is proportional to the pinhole opening area while the resolution is primarily determined by the pinhole size and detector pixel size. Compromise must be made between the resolution and exposure time. In most clinical settings, a resolution in the range of 1-2 mm will be sufficient for treatment monitoring in image-guided radiation therapy. This can be achieved by using commercial flat-panel detectors (e.g. Amorphous Silicon a-Si from Perkin-Elmer Inc.) with up to 16" detector area and 400 μm pixel size and pinholes in the range of 0.5 mm to 5 mm range. In one embodiment, an existing computed radiography (CR) flat panel detector (Konica Minolta Imaging, Inc.) is used to obtain scatter images.

In certain embodiments, additional attenuating material may be required for the pinhole collimator due to the potentially higher energy scattered radiation (compared to nuclear medicine pinhole cameras). The energy of the scattered radiation depends heavily on the angle that the pinhole camera makes with the incident treatment beam. For example, it may be wished to attenuate ~90% of the unwanted radiation. For radiation that scatters backwards into a pinhole that makes and angle of ~30° with the incident beam the scattered radiation energy would be around 200 keV and would require 0.2 cm of lead (similar to some of the higher SPECT nuclear medicine energies). For radiation that is scattering more forward into a detector making an angle of ~135° with the incident radiation beam the scattered radiation energy would be closer to 1 MeV and would require closer to 3 cm (2.87 cm) of lead. Alternatively, attenuating material of the above thickness may be placed just before a ring of pinholes, with openings for the pinholes only, to help attenuate the unwanted scatter. This would allow for more tightly packed pinhole collimators with thinner walls.

Theoretical Considerations

An initial estimate of the photons lost through scattering in soft tissue as a function of energy and scattering angle is described by the Klein-Nishina formula[15,16]. The following calculation estimates the number of scatter photons available for pinhole camera imaging from a 2 MeV mono-energetic photon beam, which is the average energy of 6 MV x-ray beams commonly used for radiation therapy.

Based on our Monte Carlo simulations, delivering 1 Gy of 6 MV beam to a Solid Water phantom (Gammex, Inc.) at the isocenter requires $4.3 \times 10^{13}$ photons/$cm^2$. The number of photons required to deliver the same dose to human subjects is similar. Based on calculation by Klein-Nishina formula, the scattering cross section is $4.7 \times 10^{-27}$ $cm^2$/steradian per free electron at 150° scattering angle (30° from vertical) and $5.8 \times 10^{-27}$ $cm^2$/steradian for 110° (70° from vertical). The energies of scattered photons are 0.27 MeV and 0.37 MeV respectively at these scattering angles. Assuming Z/A of 0.55 for water, the electron density is $0.55 \times 6.023 \times 1023 = 3.3 \times 10^{23}$/g in water. With a 4 mm diameter pinhole camera aperture placed at 16 cm from the treatment target, the camera efficiency is about $4.9 \times 10$-4 (or 0.126/162 steradian). Multiplying all these factors together, we expect, for each 1 Gy delivered to the patient at isocenter, $3.2 \times 107/cm^2$ photons at 150° scattering angle and $4.0 \times 107/cm^2$ photons at 110°, respectively. This corresponds to 105 photons per $mm^2$ pixel.

Based on the Rose criterion, a minimum signal-to-noise-ratio (SNR) of 5 is required to recognize features in radiographs[17]. The flat panel detectors generally have single photon sensitivity for keV x-rays; assuming noise by Poisson statistics, this requires at least 25 photons per pixel[17]. If we allow imperfect detector quantum efficiency and require a SNR of 10, we will need 100 photons per pixel; thus there are adequate scattered photons for every cGy delivered to the patient to provide movie-like images in real-time. This should be sufficient for monitoring of patient's anatomical structures and correcting for any movement during treatment.

Methods of Treatment

Another aspect of the present invention provides a method of treating a patient having a tumor. In one embodiment the method includes providing a radiation treatment system as disclosed herein. The patient having the tumor is placed so as to position the radiation source to deliver radiation to the region of the patient containing the tumor.

A first radiation dose is delivered to the region containing the tumor and a time series of 2-dimensional projection datasets generated from scattered radiation detected by the radiation detectors. A 3-dimensional image data set is constructed from the 2-dimensional projection datasets at each time point of the time series from the plurality of 2-dimensional projection datasets generated at that time point. The 3-dimensional image data set is indicative of the position of the region containing the tumor in relation to the radiation beam at that time point.

The 3-dimensional image data sets generated for at least two time points, for example, at successive time points, are compared and any movement of the tumor determined based on this comparison. The radiation source or the patient, or both, may then be repositioned to correct for any movement of the tumor in relation to the radiation beam and a further dose of radiation delivered to the tumor. This process may be repeated during the delivery of the prescribed radiation dose in a treatment session. Each time the tumor is observed to move out of the radiation beam, it is repositioned and the treatment continued.

In one embodiment, this process is performed in real-time, i.e. the radiation is delivered continuously and the patient and/or beam repositioned to maintain the tumor within the beam. In another embodiment, the position of the tumor may be monitored during the radiation treatment and treatment continued so long as the tumor remains within the radiation field. If the tumor moves outside the radiation field, for example due to the patient moving, or simply breathing, the radiation may be shut-off and the patient repositioned before treatment continues. In various embodiments, the 3-dimensional image data sets are compared as an interval of between, for example, 0.5-10 sec., 1-10 sec., 1-5 sec. or 1-3 sec.

The method is generally applicable for due in the treatment of a tumor, such as a lung tumor, a prostate tumor, or a liver tumor. For certain tumors, there is a difference in density between the tumor and the surrounding tissue. This difference allows for an image of the tumor, and the treatment region, to be constructed for the scattered radiation datasets. For other tumors, such a difference in density is not present. However, even in such cases, the method is applicable if a marker is present to indicate the position of the tumor.

In another embodiment, predicted temporal movement profile for the region containing the tumor is constructed before radiation treatment is performed. For example, if the movement of the tumor is expected to vary in a predictable manner, due to, for example, the patient breathing, this movement may be taken into account and the predicted temporal movement profile determined for the tumor. The radiation beam may be programmed to compensate for the patient movement.

Since the movement of the tumor may not be entirely predictable, this technique may be limited in its application. However, determination of the tumor position using the method described herein allows for the real-time revision the predicted temporal movement profile of the tumor based on the comparison of the 3-dimensional images constructed from the scattered radiation beam.

Embodiments of the invention will be further described in the following examples, which do not limit the scope of the invention described in the claims.

Example 1—Optimization of Camera Design

The pinhole camera design is optimized by modifying a pinhole camera for nuclear medicine isotope uptake studies, such as the pinhole cameras supplied by Nuclear Fields (USA) Corp., Des Planes, Ill. The aperture diameter of the preexisting camera is typically about 4 mm. Preexisting pinhole cameras are typically designed for lower energy gamma rays and would be expected to exhibit degraded performance due to increased penetration of higher energy scatter photons from scattered radiation. A series of tungsten or lead metal pinholes with sizes ranging from 0.25 mm to 5 mm is fabricated and tested. Additional lead sheets are wrapped around the camera wall to study the effect of increased radiation penetration of higher energy scatter photons[18]. Camera performance is tested for both spatial and contrast resolution using phantoms available for QA. The camera sensitivity is proportional to the aperture size and inversely proportional to the square of distance between the aperture and the object[19]. Appropriate selection of optimal imaging geometry is studied for clinically relevant conditions. For example, the imaging system initially uses a 1:1 imaging geometry with 15-20 cm target-to-pinhole distance. Other magnification ratios and imaging distances are tested during optimization studies. All measurements will be repeated several times to assure that experimental results are statistically significant.

Radiation detector sensitivity and resolution depends on a number of factors. For example, thin detectors provide better resolution but poorer sensitivity. "Off-the-shelf" detectors may require modification to work properly for this purpose. For example, a-Si flat panel is effective in detecting low energy photons but may require an electron-generating front surface screen to detect higher energy X-rays.

A computed radiography (CR) flat-panel detector (Konica Minolta Imaging, Inc.) and a-Si flat-panel detector (Perkin-Elmer Inc.) are used to obtain preliminary images. The study involves the use of various QA phantoms to measure resolution and contrast under simulated relevant clinical conditions. The detector performance is also evaluated with detective quantum efficiency (DQE) studies, which include measurements of the modulation transfer function (MTF), normalized noise power spectrum (NPS) of the imaging system, and photon fluence[20,21].

Example 2—Dose Measurements in Phantom

Figure 2A:
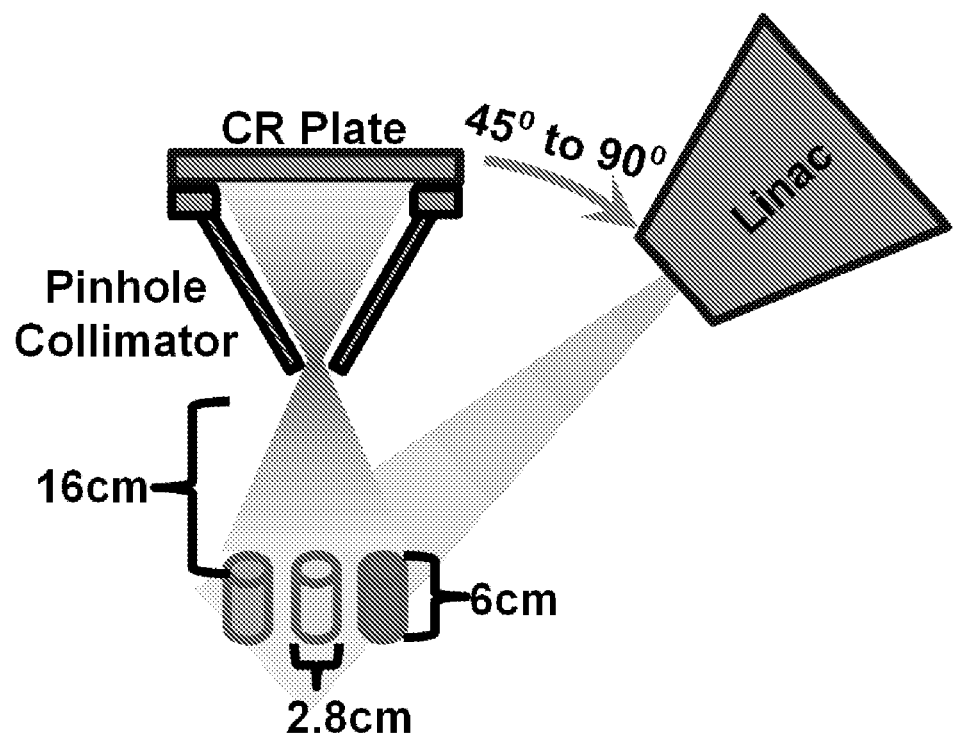
FIGS. 2(A-B) are Illustrations of the scatter imaging experimental setup and sample images. Field size is 3 cm×6 cm. Energy is 6 MV. Cylindrical phantoms are made of lung, solid water, and bone equivalent material. Scatter phantom image shown here were obtained from a 60° experimental geometry. The images clearly show the differentiation of lung, solid water (tumor), and bone materials.
Figure 2B:
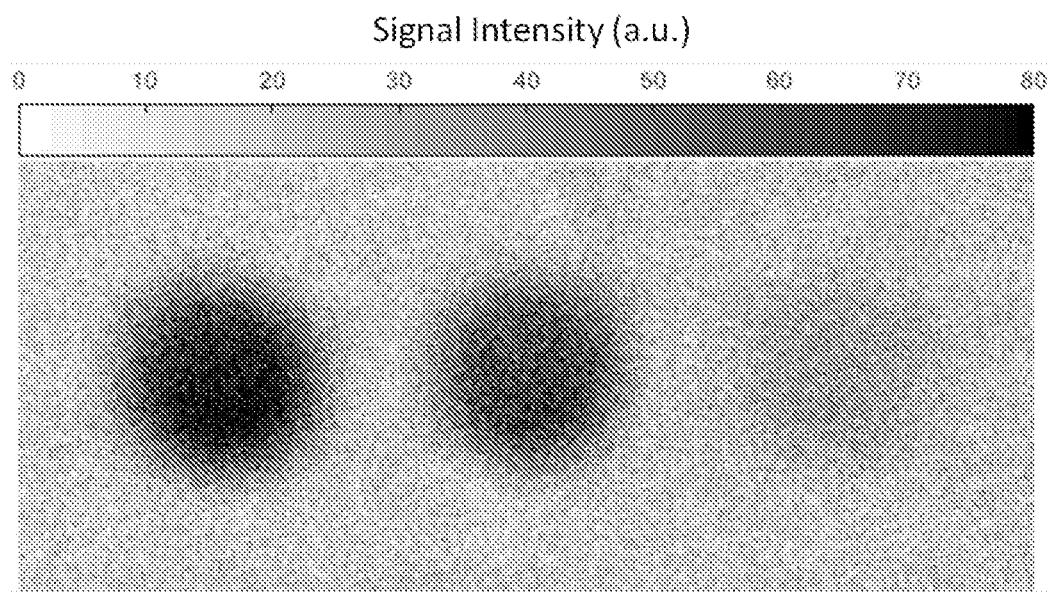

The detection setup is evaluated in the experimental set up is shown in FIG. 2. The x-ray beam is rotated about 45°-90° from the vertical axis and delivers 6 MV x-rays to 3 phantoms located near the isocenter of the linear accelerator (linac). The phantoms are 3 cylinders made of tissue equivalent materials simulating lung, soft tissue (tumor), and bone. All cylinders are of 2.8 cm in diameter and 6 cm length. A pinhole camera described in Example 1 is used for phantom measurements. The scatter photon radiation passing through the pinhole is detected by a computed radiography (CR) plate (Konica Minolta Imaging, Inc.) placed at the back of the camera. After exposure to radiation, the CR plate was fed through an image reader to process and digitize the data and display the final image on a computer workstation.

The image taken from the 60° projection angle is shown in FIG. 2. The shape of phantoms is accurately produced in the image. The three phantom images display different levels of contrast, with bone showing the greatest level of contrast and lung showing the least. This is expected as higher density material produces more scatter and a therefore larger image signal. The corresponding density scan also shows clear differentiation of the three materials.

The cylindrical phantoms are replaced with a 30×30×5 cm$^3$ solid water slab and placed an ionization chamber (Model 10×6-6 Accu-Gold, Radcal Corp.) at the level of the CR plate to measure the scatter dose there. 1.06 mGy is detected at 70° when 5 Gy of 6 MV x-ray is delivered to the phantom. This includes dose contributions from linac head leakage, transmission of phantom scatter through the wall of pinhole camera, and the scatter radiation contributing to the image signal. These measurements are repeated with the pinhole blocked by a cylindrical lead plug. The second reading (0.91 mGy) includes all radiation from the first measurement except the imaging signal. The difference between these measurements, therefore, is the radiation dose available for imaging (0.15 mGy). This corresponds to 0.03 mGy for each Gy of 6 MV x-ray beam delivered to the phantom positioned at the isocenter.

The number of photons available for imaging is calculated based on these measurements. The radiation dose from each 0.37 MeV photon scattered at 70° angle is calculated below.

$$0.37 \text{ MeV/photon} \times 10^6 \text{ mm}^2/\text{m}^2 \times 1.6 \times 10^{-13} \text{ J/MeV} \times 0.0033 \text{ m}^2/\text{kg} = 1.95 \times 10^{-10} \text{ Gy-mm}^2/\text{photon}$$

where $1.6 \times 10^{-13}$ J/MeV is MeV to joule conversion and 0.0033 m$^2$/kg is the mass energy absorption coefficient for 0.37 MeV photons in water. Dividing this into 0.03 mGy, the number of photons from each Gy delivered to isocenter is, therefore, $1.54 \times 10^5$ photons/mm$^2$. While less than the $4.0 \times 10^5$ photons/mm$^2$ predicted from theoretical calculations, these measurements confirm that there are sufficient photons available for imaging. Differences from theoretical calculations are likely attributable to the simplicity of the theoretical model and the possibilities that the lead plug imperfectly blocked the pinhole.

Example 3—Phantom Design and Construction

Several special purpose phantoms are designed for calibration and quality assurance testing of radiation therapy treatment machines and CT systems. These include cylindrical phantoms with inserts simulating tissues with density ranging from low density soft tissue to high density bones, a Las Vegas phantom for resolution and contrast QA tests[22], CATPHAN phantom for QA tests of CT[23], and a PIPSPRO phantom for general imaging QA (Standard Imaging, Inc.).

Figure 3:
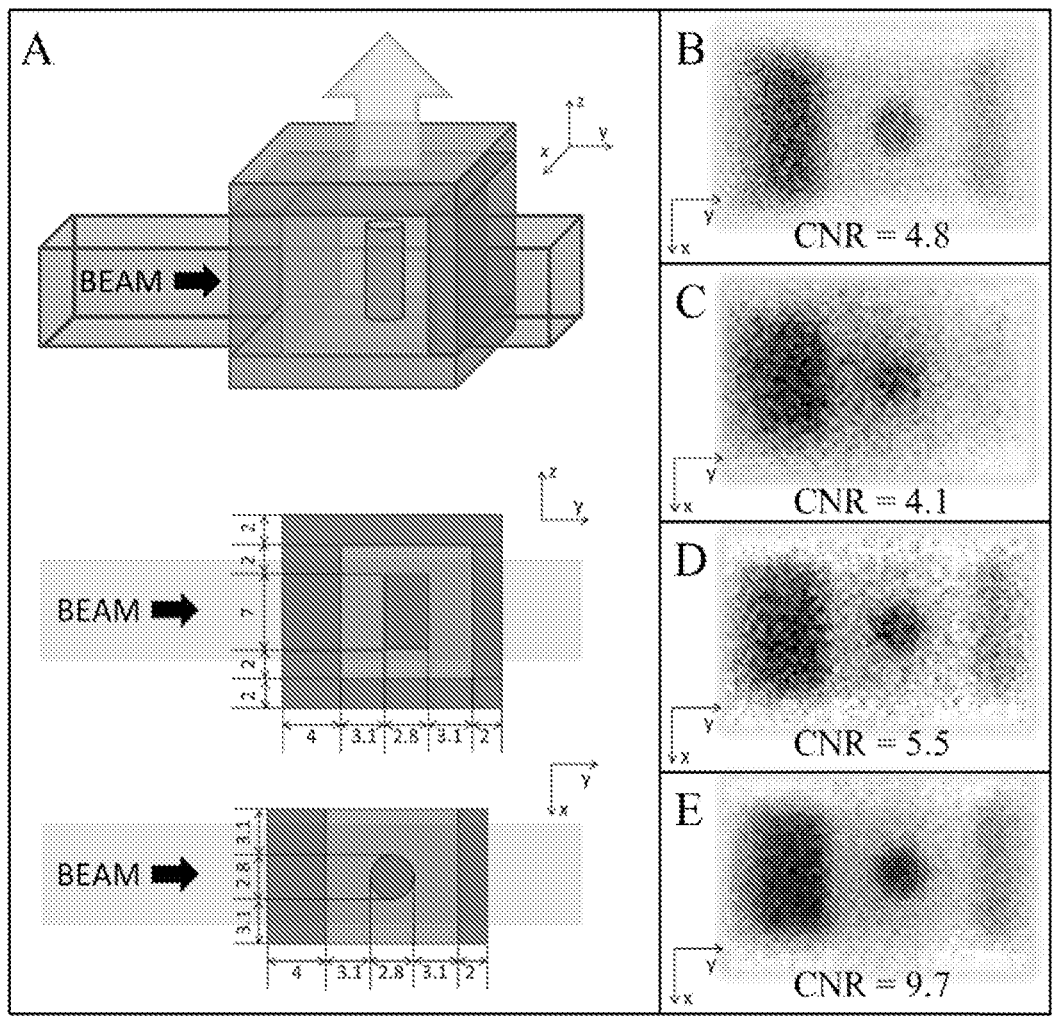
FIGS. 3(A-E) are schematic diagrams of a complex lung tumor phantom simulated in MCNP and constructed for experiments.

As an example, FIG. 3 shows a phantom constructed for a feasibility study; it included unit density materials (simulating chest wall) surrounding a low density lung volume with an embedded soft tissue density tumor. We have performed both Monte Carlo simulations and measurements to illustrate the feasibility of this study. In addition, we will construct a dynamic phantom with a movable soft tissue tumor to test the effect of breathing motion on the scatter images. The simulated tumor will be imaged at different depths to cover the range of possible tumor locations encountered in clinical practice.

In addition to analysis of QA phantom images, the imaging system performance is evaluated with Detective Quantum Efficiency (DQE) studies which require the measurement of Modulation Transfer Function (MTF), Noise Power Spectrum (NPS) and photon fluence. Briefly, the MTF is calculated from Line Spread Function (LSF) which is measured by differentiating a tungsten edge profile obtained close to the center of the field of view. This are measured both under unit density and 0.2-0.3 low density background, simulating soft tissue and lung environment. A uniform density slab solid water phantom is used to produce images used for noise power spectrum analysis. As there may be artifacts in the images, images are measured twice for each set up. Most artifacts are structural and can be removed by subtracting one from the other paired images. Small reference BB markers are used during imaging to assure the proper registration of images prior to subtraction. Difference images for each paired uniform density images are used to calculate NPS. Photon fluence is measured with the same ionization chamber system used previously. The DQE analysis is aided by available research software tools[21].

Example 4—Environmental Effects Study

In additional to treatment beams and patient scatter, there are other sources of radiation in the radiation treatment room. These include leakage radiation from the head of the treatment linac and the scatter off the collimator. The magnitude and direction of radiation from these sources depend on the location of the scatter detector, field size of the treatment beam, and gantry angle of treatment machine.

Simulated lung tumors are placed in a humanoid phantom. The placement of tumor covers various peripheral and central locations within the lung. The effect of these environmental parameters on scatter imaging and design strategies is estimated to correct for these effects if needed. For example, in the event that head leakage and collimator scatter is significant in certain combinations of tumor location and gantry positions, strategically repositioning the pinhole camera and/or placing shielding blocks can potentially reduce or eliminate these undesirable effects.

Example 5—Image Construction and Optimization

Figure 4:
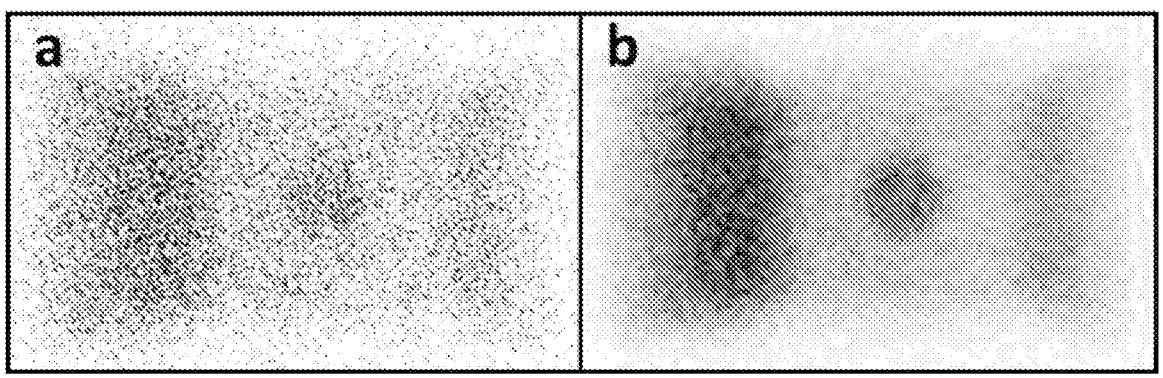
FIGS. 4(A-B) show plots illustrating scatter image processing.

The scatter image is further enhanced using various methods such as background subtraction, pixel averaging, histogram equalization, edge enhancement etc. to maximize image quality. This is accomplished by using resolution and contrast phantom images. Indices such as signal noise ratio (SNR) and contrast noise ratio (CNR) are used to evaluate the degree of image enhancement. Examples of image enhancement after pixel averaging are shown in FIG. 4. Both SNR and CNR improve by more than 12 fold from pixel averaging in this case. Clear visualization of these materials confirms scatter imaging's capabilities. Furthermore, the use of digitally reconstructed radiographs (DRR) from existing patient CT images is studied. These DRRs are reconstructed along the same direction of projection for the particular scatter radiograph and provide a priori knowledge for it[24]. Image fusion between the DRR and corresponding scatter radiograph may further improve the visualization of the scatter images[25,26]. Software (MIMvista; Mirada) may facilitate this area of research.

During treatment, the treatment beam energy may be varied, for example, between 6 MV to 18 MV and the detection angle may be varied, for example, between 15 and 90 degrees from the vertical axis. This is of interest as the scatter cross-section varies with treatment beam energy and angle. Low energy scatter photons may be adequate for superficial targets whereas higher energy scatter may be more appropriate for deeper lesions. Features of interest for resolution and contrast phantom are placed over depth range of 1-10 cm. Resolution and contrast vs depth relationships are established for each energy. Effects of exposure time as related to image quality will be measured for each setting. Effects of scatter are analyzed by repeating the above studies for radiation field size from 3×3-15×15 cm$^2$, covering range of tumor size encountered for stereotactic ablation lung cancer treatments.

Scatter images have been used to provide 3-D attenuation maps for SPECT imaging using various methods, including dual detector back projection[27] and iterative algorithms[28], among others. Multiple pinhole cameras are used to produce stereoscopic scatter images that can be used to reconstruct the 3-D profile of the irradiated volume. In order to develop and implement methods that will enable 3-D image reconstruction from scatter images acquired from multiple angles, it is necessary to first determine a mathematical model to describe the physics behind the formation of a single planar scatter image. We consider the problem as discrete-to-discrete. The formation of a projected image is mathematically represented as $$\vec{g} = H\vec{f}$$

where $\vec{g}$ is a vector containing the data from all of the pixels or detector elements (dj) in the 2-D projection, $\vec{f}$ is a vector containing the data from each voxel (vk) in the 3-D image, and H is the system matrix describing how each voxel contributes to each pixel.

Figure 5:
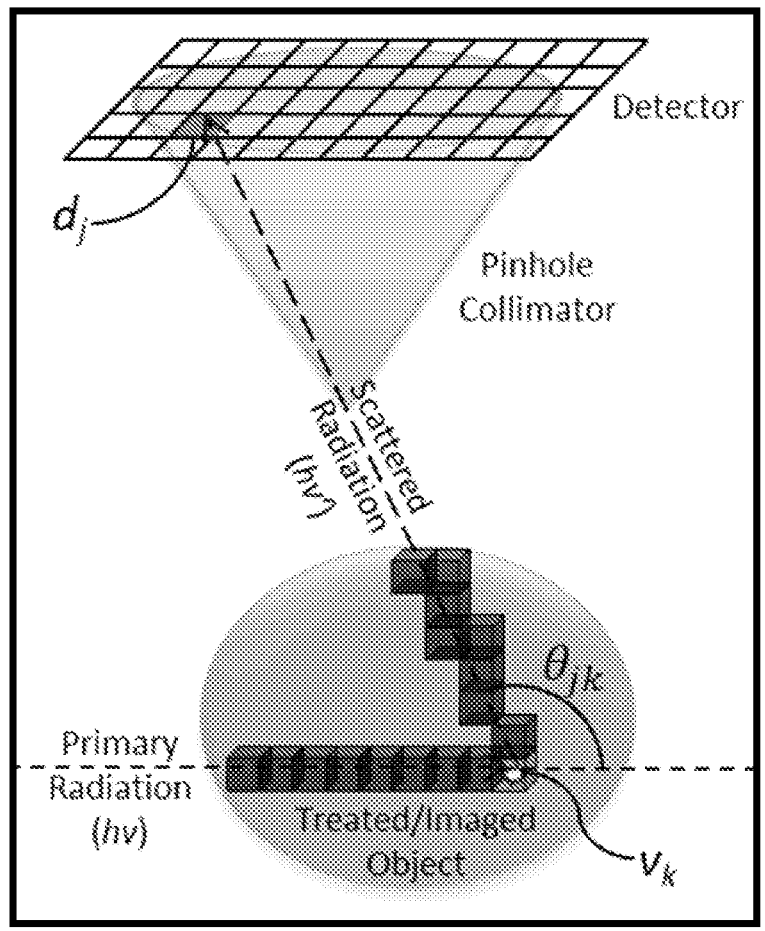
FIG. 5 is a schematic diagram illustrating a scatter image analytic model.

FIG. 5 illustrates what is considered to formulate H. It includes the attenuation of the treatment beam intensity at each voxel (vk) by the overlying materials, energy and Klein-Nishina differential cross section for Compton scatter at that voxel, attenuation of scatter intensity before reaching the pinhole, and the detection of photons at the detector element dj through the particular pinhole geometry used. Alternatively, dose distribution information from the patient treatment plan can provide a surrogate measure of the probability of a Compton interaction in each voxel, thus eliminating the need for initial treatment beam intensity attenuation considerations.

Once the matrix H has been determined based on the above considerations and using prior information from planning CT images, optimization-based reconstruction methods is implemented to form meaningful 3-D images using a limited number of 2-D projections. This is important due to logistic constraints regarding the placement of multiple pinhole camera detectors around the treatment machine. Promising results for similar problems in fan beam CT[29] as well as cone beam CT[30] image reconstruction are achieved using iterative reconstruction algorithms based on the minimization of total variation. Optimization programs are developed to find the solution $\vec{f}^*$ that minimizes the total variation (TV, or L1 norm of the gradient image, which has been exploited as a sparsity constraint for potentially narrowing the solution space):

$$\vec{f}^* = \mathrm{argmin} \|\vec{f}\|_{TV}$$

such that:

$$|H\vec{f} - \vec{g}| \leq \varepsilon$$

$$f_k \geq 0$$

where $\varepsilon > 0$ is a selected parameter for accommodating possible inconsistency between data and imaging model.
In solving the above optimization program, an adaptive steepest-descent and projection-onto-convex-set (ASD-POCS)-type algorithm[31] is extended from that developed for CT. An estimate of the object support and parameter $\varepsilon$ may be used for reducing reconstruction artifacts. To gain algorithm efficiency, the Nesterov's step-size[32] adjustments are exploited to obtain nearly optimal convergence rates. In particular, algorithms for solving the optimization program by deriving new primal-dual algorithms based on the Chambelle-Pock framework[33] considerably reduce artifacts from data noise and other inconsistencies in the proposed imaging system. Inverse-crime studies are used to validate the development and implementation of the algorithms using simulated data.

Example 6—Scatter Imaging System for Lung Stereotactic Body Radiation Therapy (SBRT)

FIG. 6 illustrates a scatter imaging system for lung Stereotactic Body Radiation Therapy (SBRT). Incident primary radiation from lateral beam shown and scatter detected by anterior pinhole camera. A flat panel detector is used to form an image of the patient anatomy using the scattered radiation.

Example 7—Scatter Images of Cylindrical Phantoms

Figure 7:
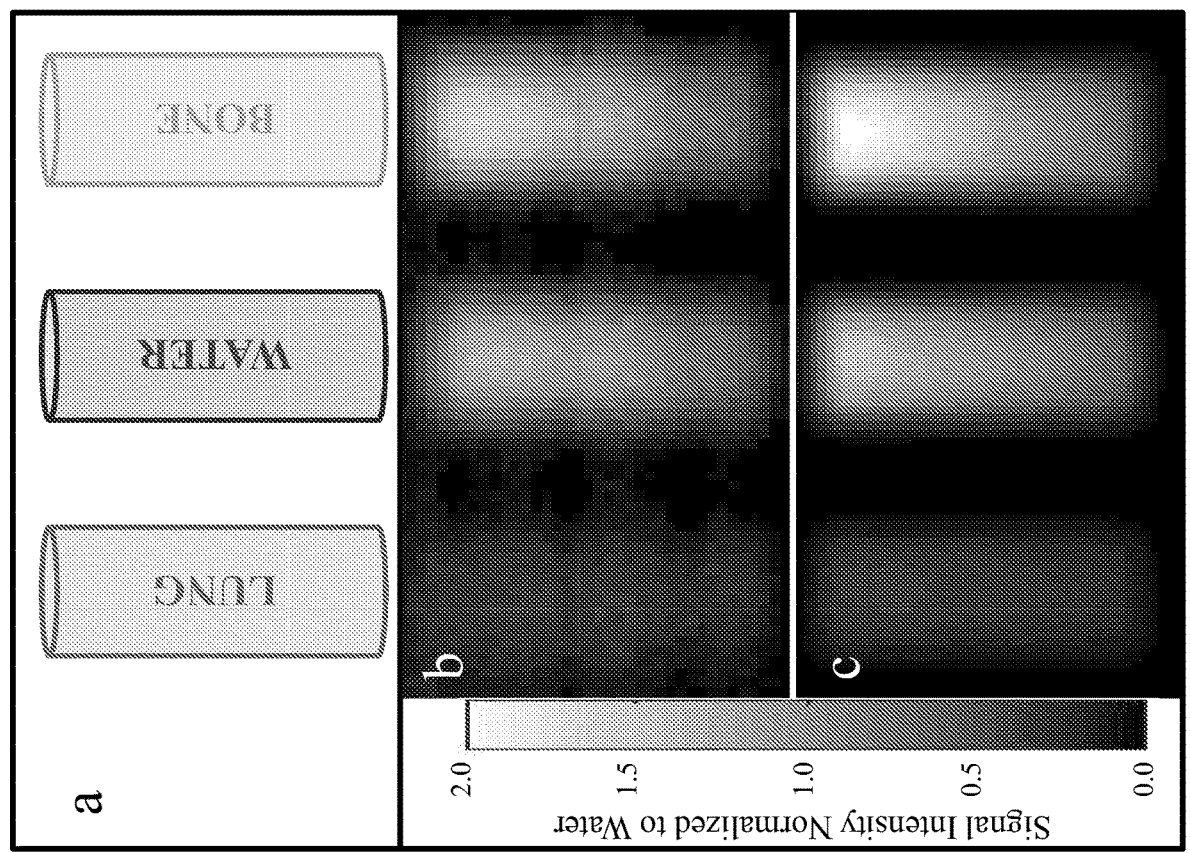
FIGS. 7(A-C) are illustrations of scatter images of cylindrical phantoms of clinically relevant compositions.

FIG. 7 shows scatter images of cylindrical phantoms of clinically relevant compositions FIG. 7(A) agree both qualitatively and quantitatively for the FIG. 7(B) experimental and FIG. 7(C) simulated images. The treatment beam direction is from the top of the figures and the pinhole camera axis is perpendicular to the page.

Example 8—Diagram of Lung Tumor Phantom

Figure 8:
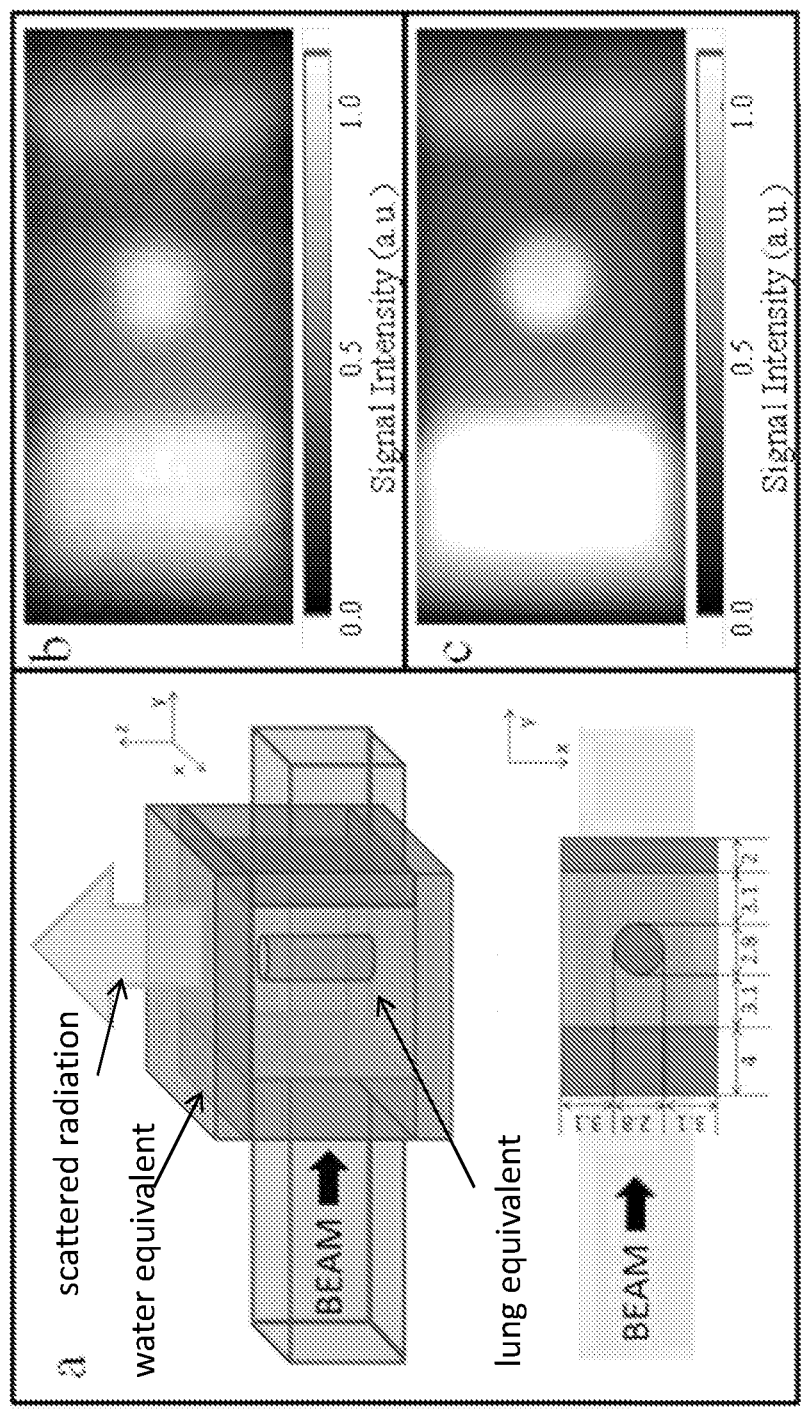
FIGS. 8(A-C) are schematic diagrams of a lung tumor phantom that has been experimentally imaged and simulated using Monte Carlo N-Particle (MCNP).

FIG. 8(A) is a schematic diagram of a lung tumor phantom that has been experimental imaged and simulated using Monte Carlo N-Particle (MCNP). Blue (outer square box) and orange (inner square box) materials are water equivalent (solid water and bolus) and lung equivalent (cork), respectively. The phantom simulates a 2.8 cm diameter cylinder oriented so that the incident radiation beam (red) passes through 4 cm of chest wall and 3.1 cm of lung. On the detector side of the phantom (90° from beam axis) the scattered radiation (yellow) passes through 2 cm of lung and 2 cm of chest wall. This geometry approximates that which may be encountered in a lung SBRT treatment. In FIG. 8(B) the experimental (5000 MU or 250 second) image can be seen to match closely with the Noiseless MCNP simulated image of the same phantom FIG. 8(C). Quantitatively these images show similar tumor-to-lung contrast (relative to tumor signal): 0.52±0.03 and 0.57±0.04 for the experimental and simulated images respectively.

Example 9—Experimental Images of the Lung Tumor Phantom

Figure 9:
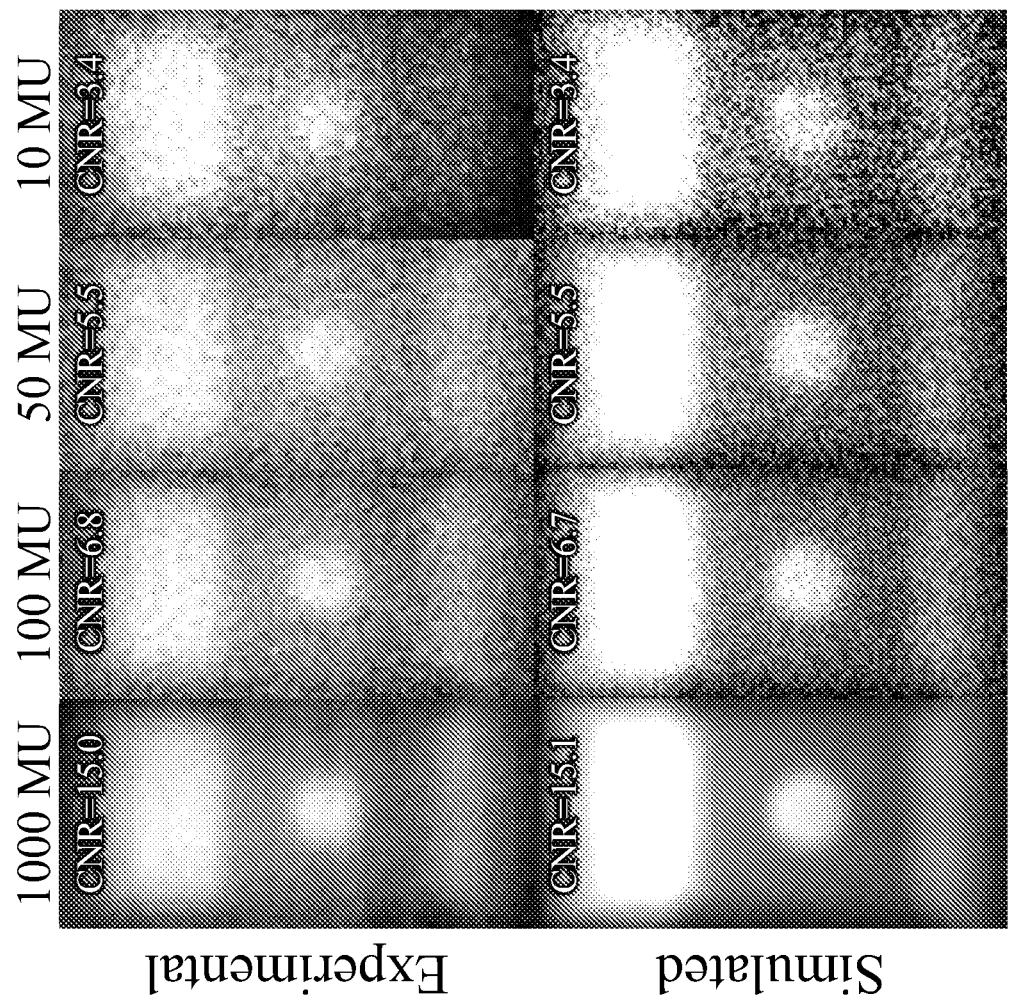
FIG. 9 shows experimental and simulated images of the lung tumor phantom and their respective CNR. Experimental images are acquired using different MU using a dose rate of 1200 MU/min. Random Gaussian noise of varying amplitude was added to simulated images to match CNR values from corresponding experimental images.

FIG. 9 shows experimental and simulated images of the lung tumor phantom. Experimental images are acquired using different MU using a dose rate of 1200 MU/min. Appropriate amount of random Gaussian noise is added to the noise free simulated images to match CNR values from corresponding experimental images. These are demonstrated by the bottom row images of equivalent CNR values (the beam is from the top of the page).

Figure 10:
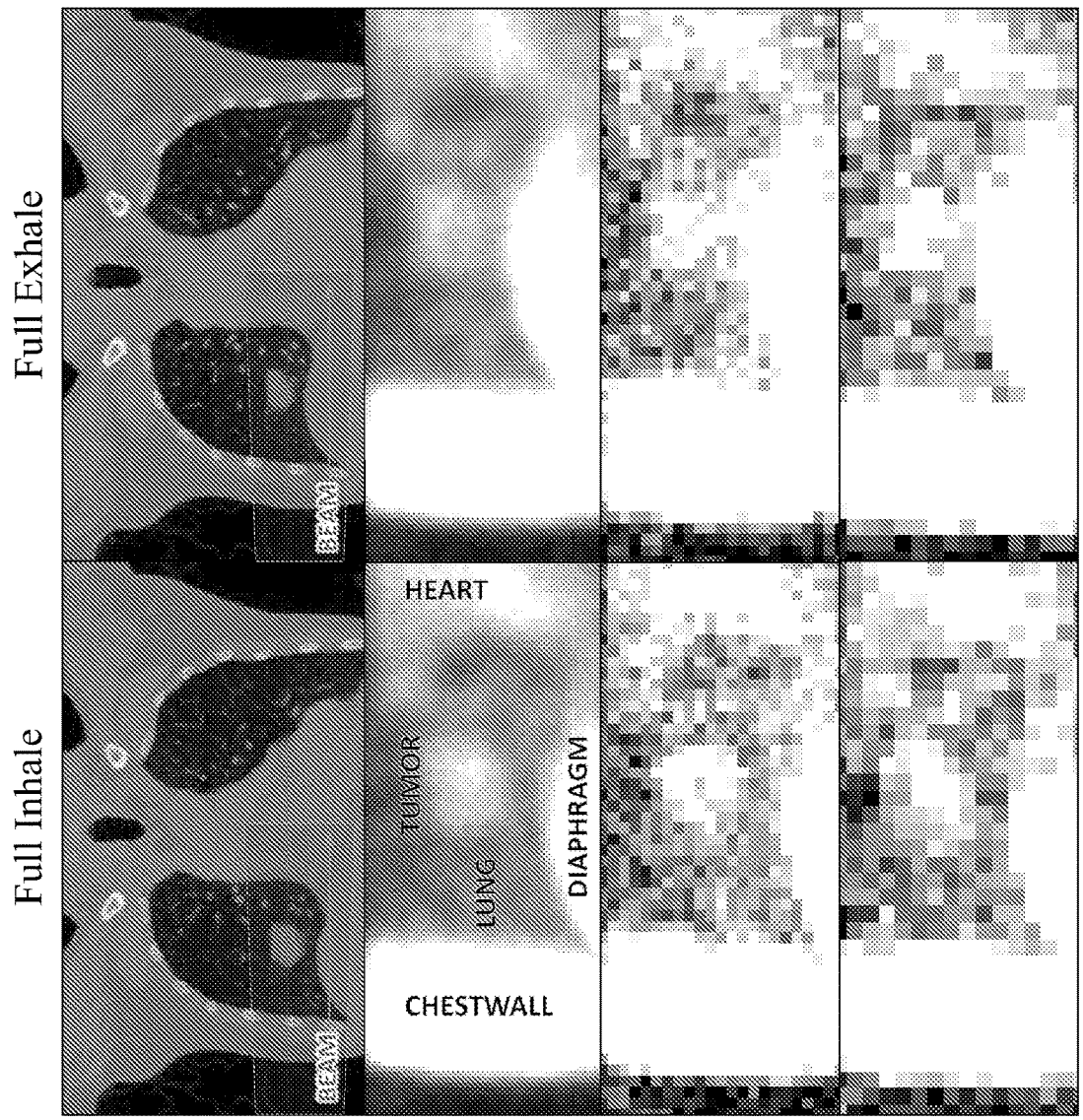
FIG. 10 shows the simulation of patient scatter images using real patient 4DCT data as digital phantom in MCNP simulation. Significant relative geometry difference between tumor and diaphragm is observed for full inhale and exhale images.

Example 10—Simulation of Patient Scatter Images Using Real Patient 4DCT Data FIG. 10 shows the simulation of patient scatter images using real patient 4DCT data as digital phantom in MCNP simulation. The left column shows images from the full inhalation phase and the right column shows images from the full exhale phase. The first row is a coronal slice from the 4DCT images showing the simulated treatment beam placement and tumor location. The second row shows noiseless simulated scatter images, demonstrating appreciable contrast between lung and surrounding tumor. The third row shows simulated images with noise added mimicking a 50 MU or 2.5 second acquisition and giving a CNR~3.2 (2×2 pixel region averaged to reduce noise). The fourth row shows simulated images with noise added mimicking a 10 MU or 0.5 second acquisition and giving a CNR~2.7 (3×3 pixel region averaged to reduce noise). This demonstrates that scatter imaging has the potential to provide subsecond images of patient anatomy during SBRT treatments. Appreciable change in tumor/diaphragm geometry is observed between inhale and exhale images.

REFERENCES

1 "Cancer Facts and Statistics 2014," 2014.
2 Timmerman, Robert Paulus, Rebecca Galvin, James Michalski, Jeffrey Straube, William Bradley, Jeffrey Fakiris, Achilles Bezjak, Andrea Videtic, Gregory Johnstone, David Fowler, Jack Gore, Elizabeth Choy, Hak, "Stereotactic body radiation therapy for inoperable early stage lung cancer." JAMA: the Journal of the American Medical Association 303, 1070-1076 (2010).
3 Shirvani, Shervin Jiang, Jing Chang, Joe Welsh, James Gomez, Daniel Swisher, Stephen Buchholz, Thomas Smith, Benjamin, "Comparative effectiveness of 5 treatment strategies for early-stage non-small cell lung cancer in the elderly." Int. J. Radiat. Oncol. Biol. Phys. 84, 1060-1070 (2012).
4 Field, John Aberle, Denise Altorki, Nasser Baldwin, David Dresler, Carolyn Duffy, Stephen Goldstraw, Peter Hirsch, Fred Pedersen, Jesper de Koning, Harry Mulshine, James Sullivan, Daniel Tsao, Ming-Sound Travis, William, "The International Association Study Lung Cancer (IASLC) Strategic Screening Advisory Committee (SSAC) Response to the USPSTF Recommendations." Journal of thoracic oncology 9, 141-143 (2014).
5 Aberle, Denise Adams, Amanda Berg, Christine Black, William Clapp, Jonathan Fagerstrom, Richard Gareen, Ilana Gatsonis, Constantine Marcus, Pamela Sicks, JoRean, "Reduced lung-cancer mortality with low-dose computed tomographic screening." N. Engl. J. Med. 365, 395-409 (2011).
6 J. E. Marks, A. G. Haus, M. L. Sutton, M. L. Griem, "Localization error in the radiotherapy of Hodgkin's disease and malignant lymphoma with extended mantle fields," Cancer, 83-90 (1974).
7 B. Loo, "Stereotactic ablative radiotherapy (SABR) for lung cancer: What does the future hold?" Journal of Thoracic Disease 3, 150-152 (2011).
8 L. I. Cervino and S. B. Jiang, "Intrafraction variations and management technologies," in Adaptive Radiation Therapy, edited by X. A. Li (CRC Press, Boca Raton, Fla., 2011), pp. 203-216.
9 P. G. Lale, "The examination of internal tissues, using gamma-ray scatter with a possible extension to megavoltage radiography." Physics in medicine biology 4, 159-67 (1959).
10 R. L. Guzzardi G., "A critical review of Compton imaging." Crit. Rev. Biomed. Eng. 15, 237-268 (1987).
11 G. H. Harding E., "Compton scatter imaging: A tool for historical exploration." Applied radiation and isotopes 68, 993-1005 (2010).
12 Smith, Benjamin Smith, Grace Hurria, Arti Hortobagyi, Gabriel Buchholz, Thomas, "Future of cancer incidence in the United States: burdens upon an aging, changing nation." Journal of clinical oncology 27, 2758-2765 (2009).
13 De Los Santos, Jennifer Popple, Richard Agazaryan, Nzhde Bayouth, John Bissonnette, Jean-Pierre Bucci, Mary Dieterich, Sonja Dong, Lei Forster, Kenneth Indelicato, Daniel Langen, Katja Lehmann, Joerg Mayr, Nina Parsai, Ishmael Salter, William Tomblyn, Michael Yuh, William T C Chetty, Indrin, "Image guided radiation therapy (IGRT) technologies for radiation therapy localization and delivery." Int. J. Radiat. Oncol. Biol. Phys. 87, 33-45 (2013).
14 P. Keall, "Methods for real-time tumor position monitoring and radiotherapy tracking," in Adaptive Radiation Therapy, edited by X. A. Li (CRC Press, Boca Raton, Fla., 2011), pp. 217-228.
15 O. Klein and Y. Nishina, "Über die Streuung von Strahlung durch freie Elektronen nach der neuen relativistischen Quantendynamik von Dirac," Z. Phys 52, 853-869 (1929).
16 S. Weinberg, "The Quantum Theory of Fields," in the Quantum Theory of Fields, Vol. I, edited by Anonymous (Cambridge University Press, Canbridge, UK, 1995), pp. 362-369.
17 A. Rose, "Unified approach to performance of photographic film, television pickup tubes, and human eye," Journal of the Society of Motion Picture Engineers 47, 273-294 (1946).
18 Smith, M F Jaszczak, R J., "The effect of gamma ray penetration on angle-dependent sensitivity for pinhole collimation in nuclear medicine." Med. Phys. 24, 1701-1709 (1997).
19 H. H. Barrett and W. Swindell, Radiological Imaging: The Theory of Image Formation, Detection, and Processing Vol. 1 & 2 (Academic Press, New York, 1981).
20 E. Samei and M. J. Flynn, "An experimental comparison of detector performance for direct and indirect digital radiography systems," Med. Phys. 30, 608-622 (2003).
21 B. Donini, S. Rivetti, N. Lanconelli, M. Bertolini, "Free software for performing physical analysis of systems for digital radiography and mammography," Med. Phys. 41 (2014).
22 Herman, M G Balter, J M Jaffray, D A McGee, K P Munro, P Shalev, S Van Herk, M Wong, J W., "Clinical use of electronic portal imaging: report of AAPM Radiation Therapy Committee Task Group 58." Med. Phys. 28, 712-737 (2001).
23 "The Phantom Laboratory," Salem, N.Y., USA.
24 Y. Zhang, F. Yin, W. P. Segars, L. Ren, "A technique for estimating 4D-CBCT using prior knowledge and limited angle projections," Med. Phys. 40 (2013).
25 J. Cai, J. C. Chu, D. Recine, M. Sharma, C. Nguyen, R. Rodebaugh, V. A. Saxena, A. Ali, "CT and PET lung image registration and fusion in radiotherapy treatment planning using the chamfer-matching method." Int. J. Radiat. Oncol. Biol. Phys. 43, 883-891 (1999).
26 Y. Zhang, J. C. H. Chu, W. Hsi, A. J. Khan, P. S. Mehta, D. B. Bernard, R. A. Abrams, "Evaluation of four volume-based image registration algorithms," Medical Dosimetry 34, 317-322 (2009).
27 D. W. Mundy and M. G. Herman, "An accelerated threshold-based back-projection algorithm for Compton camera image reconstruction," Med. Phys. 38, 15-22 (2011).
28 Cade, Sarah Arridge, Simon Evans, Martyn Hutton, Brian, "Use of measured scatter data for the attenuation correction of single photon emission tomography without transmission scanning." Med. Phys. 40, 082506-082506 (2013).
29. Sidky E, Kao C, Pan X. Accurate image reconstruction from few-views and limited-angle data in divergent-beam CT. J Xray Sci Technol. 2006; 14:119-139.
30. Sidky E, Pan X. Image reconstruction in circular cone-beam computed tomography by constrained, total-variation minimization. Phys Med Biol. 2008; 53:4777-4807.
30. Han X, Bian J, Ritman E L, Sidky E Y, Pan X. Optimization-based reconstruction of sparse images form few-view projections. Phys Med Biol. 2012; 57(16):5245-5273.
32. Nesterov Y. Smooth minimization of non-smooth functions. Math Program. 2005; 103(1, Ser. A):127-152.
33. Chambolle A, Pock T. A first-order primal-dual algorithm for convex problems with applications to imaging. J Math Imaging Vis. 2011; 40:120-145.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:
1. A radiation treatment system comprising:
a patient positioning structure for positioning a patient having a tumor;
a radiation source device positioned to deliver a radiation beam upon a region containing the tumor in the patient positioned on the patient positioning structure;
a plurality of radiation detectors positioned in an array to detect scattered radiation from the region, wherein each of the plurality of radiation detectors is configured to acquire a 2-dimensional projection dataset from radiation scattered from the region, and the plurality of radiation detectors are positioned on a surface of a sphere centered on the tumor;

a processing unit operatively connected to each of the plurality of radiation detectors and configured to receive the 2-dimensional projection dataset from each of the plurality of radiation detectors and to generate a 3-dimensional image dataset from the 2-dimensional projection datasets from the plurality of radiation detectors.

2. The system of claim 1, wherein each of the plurality of radiation detectors comprise a pinhole collimator and a radiation detection panel.

3. The system of claim 1, wherein the array comprises at least 3 radiation detectors.

4. The system of claim 3, wherein the array comprises between 3 and 60 radiation detectors.

5. The system of claim 4, wherein the array comprises between 10 and 30 radiation detectors.

6. The system of claim 1, wherein the plurality of radiation detectors are positioned at angles of between 15 and 165 with respect to the radiation beam.

7. The system of claim 2, wherein the radiation detectors are positioned so as to achieve a 1:1 imaging geometry and wherein front surfaces of the pinhole collimators are positioned at a distance of between 12 and 25 cm from a center of the tumor.

8. The system of claim 2, wherein each of the plurality of pinhole collimators have an axis aligned so as to extend through a center of the tumor.

9. A method of treating a patient having a tumor, comprising:
  (i) providing a radiation treatment system comprising:
    a radiation source device positionable to deliver a radiation beam upon a region of the patient containing the tumor;
    a plurality of radiation detectors positioned in an array on a surface of a sphere centered on the tumor to detect radiation scattered from the region, wherein each of the plurality of radiation detectors is configured a acquire a 2-dimensional projection dataset from a portion of the scattered radiation;
    a processing unit operatively connected to each of the plurality of radiation detectors and configured to receive the 2-dimensional projection dataset from each of the plurality of radiation detectors and to generate a 3-dimensional image dataset from the 2-dimensional projection datasets;
  (ii) positioning the radiation source to deliver radiation to the region;
  (iii) delivering a first radiation dose to the region;
  (iv) generating a time series of 2-dimensional projection datasets from scattered radiation detected by the plurality of radiation detectors;
  (v) generating a 3-dimensional image data set at each time point of the time series from the plurality of 2-dimensional projection datasets generated at that time point, wherein the 3-dimensional image data set at a time point is indicative of the position of the region in relation to the radiation beam at that time point;
  (vi) comparing the 3-dimensional image data sets generated for at least two time points;
  (vii) determining a movement of the region in relation to the radiation bean on the basis of the comparing;
  (viii) repositioning the radiation source or the patient to correct for any movement of the region in relation to the radiation beam; and
  (ix) delivering a second radiation dose to the region.

10. The method of claim 9, wherein the tumor is selected from the group consisting of a lung tumor, a prostate tumor, and a liver tumor.

11. The method of claim 9, wherein the comparing is at an interval of between 0.5 seconds and 10 seconds.

12. The method of claim 9, further comprising positioning a marker within the tumor, wherein the marker is observable in the 3-dimensional image dataset.

13. The method of claim 9, wherein each of the plurality of radiation detectors comprise a pinhole collimator and a radiation detecting panel.

14. A method of treating a patient having a tumor, comprising:
  (i) providing a radiation treatment system comprising:
    a radiation source device positionable to deliver a radiation beam upon a region of the patient containing the tumor;
    a plurality of radiation detectors positioned in an array on a surface of a sphere centered on the tumor to detect radiation scattered from the region, wherein each of the plurality of radiation detectors is configured a acquire a 2-dimensional projection dataset from a portion of the scattered radiation;
    a processing unit operatively connected to each of the plurality of radiation detectors and configured to receive the 2-dimensional projection dataset from each of the plurality of radiation detectors and to generate a 3-dimensional image dataset from the 2-dimensional projection datasets;
  (ii) generating a predicted temporal movement profile for the region;
  (iii) positioning the radiation source to deliver radiation to the region;
  (iv) delivering a first radiation dose to the region at a first time point;
  (v) repositioning, based on the predicted temporal movement profile of the region at a second time point, the radiation source or the patient to deliver a second radiation dose at the second time point;
  (vi) generating a 2-dimensional projection dataset from scattered radiation detected by each of the plurality of radiation detectors at the second time point;
  (vii) generating a 3-dimensional image data set at the second time point from the plurality of 2-dimensional projection datasets generated at the second time point, wherein the 3-dimensional image data set at the second time point is indicative of the position of the region in relation to the radiation beam at the second time point;
  (viii) comparing the position of the region as determined by the 3-dimensional image data set at the second time point with the predicted temporal movement profile for the region at the second time point;
  (ix) revising the predicted temporal movement profile of the region based on the comparing; and
  (x) repositioning, based on the revised predicted temporal movement profile of the region at a third time point, the radiation source or the patient to deliver a third radiation dose at the third time point.

15. The method of claim 14, wherein the interval between the first and second time points is between 0.5 seconds and 10 seconds.

16. The method of claim 15, wherein the interval between the first and second time points is between 1.0 seconds and 3 seconds.

17. The method of claim 14, further comprising positioning a marker within the tumor, wherein the marker is observable in the 3-dimensional image dataset.

18. The method of claim 14, wherein the tumor is selected from the group consisting of a lung tumor, a prostate tumor, and a liver tumor.

19. The method of claim 9, wherein the repositioning occurs at multiple times during delivery of treatment.

* * * * *